(12) United States Patent
Saito et al.

(10) Patent No.: US 9,907,541 B2
(45) Date of Patent: Mar. 6, 2018

(54) STOOL COLLECTION CONTAINER

(71) Applicants: EIKEN KAGAKU KABUSHIKI KAISHA, Tokyo (JP); TOYO SEIKAN CO., LTD., Shinagawa-ku, Tokyo (JP)

(72) Inventors: Shingo Saito, Tokyo (JP); Wataru Suzuki, Tochigi (JP); Hiroaki Hayashi, Yokohama (JP); You Yamamori, Yokohama (JP); Yasuyuki Takeuchi, Yokohama (JP)

(73) Assignees: EIKEN KAGAKU KABUSHIKI KAISHA, Tokyo (JP); Toyo Seikan Co., Ltd., Tokyo (JP)

( * ) Notice: Subject to any disclaimer, the term of this patent is extended or adjusted under 35 U.S.C. 154(b) by 0 days.

(21) Appl. No.: 14/913,781

(22) PCT Filed: Aug. 19, 2014

(86) PCT No.: PCT/JP2014/004215
§ 371 (c)(1),
(2) Date: Feb. 23, 2016

(87) PCT Pub. No.: WO2015/029369
PCT Pub. Date: Mar. 5, 2015

(65) Prior Publication Data
US 2016/0278744 A1    Sep. 29, 2016

(30) Foreign Application Priority Data
Aug. 26, 2013 (JP) ................................ 2013-174530

(51) Int. Cl.
*B01L 3/14* (2006.01)
*A61B 10/00* (2006.01)
(Continued)

(52) U.S. Cl.
CPC .......... *A61B 10/0038* (2013.01); *B01D 35/02* (2013.01); *B01L 3/50825* (2013.01);
(Continued)

(58) Field of Classification Search
CPC .............................. B01L 3/5023; B01L 3/5029
(Continued)

(56) References Cited

U.S. PATENT DOCUMENTS

| 5,514,341 A | 5/1996 | Urata et al. |
| 5,882,942 A | 3/1999 | Kagaya |

(Continued)

FOREIGN PATENT DOCUMENTS

| JP | 6-186227 A | 7/1994 |
| JP | 712808 A | 1/1995 |

(Continued)

OTHER PUBLICATIONS

International Preliminary Report dated Mar. 10, 2016, issued by the International Bureau in corresponding International Application No. PCT/JP2014/004215.
(Continued)

*Primary Examiner* — Natalia Levkovich
(74) *Attorney, Agent, or Firm* — Sughrue Mion, PLLC (57) ABSTRACT

A stool container is provided with a lid body (2) having a lid part (2a) for sealing a container and a stool collection rod (2b) for collecting stool, a cylindrical container body (3) that has a liquid reservoir (3b) formed at the distal end thereof via a filter holding part (3a) and has an open proximal end, and an inner plug 4 that is inserted from the proximal end of the container body (3) in to the container body (3). The distal end of the inner plug (4) has a bottom surface (4a) that is orthogonal to the longitudinal direction and, in the center of the bottom surface (4a), a scraping part (4b) through which the stool collection rod (2b) can be inserted. A stool collection rod guide part is formed that comprises a plurality of sloping ribs (4c) disposed radially around the scraping part (4b).

2 Claims, 8 Drawing Sheets

(51) Int. Cl.
*B01D 35/02* (2006.01)
*B01L 3/00* (2006.01)

(52) U.S. Cl.
CPC ..... *B01L 2200/14* (2013.01); *B01L 2300/042* (2013.01); *B01L 2300/06* (2013.01); *B01L 2300/0609* (2013.01); *B01L 2300/0681* (2013.01); *B01L 2300/0832* (2013.01)

(58) Field of Classification Search
USPC .................................................. 422/549, 550
See application file for complete search history.

(56) References Cited

U.S. PATENT DOCUMENTS

| | | | |
|---|---|---|---|
| 6,299,842 B1 * | 10/2001 | Kozak | A61B 10/0038 422/550 |
| 2011/0130681 A1 | 6/2011 | Okumura et al. | |

FOREIGN PATENT DOCUMENTS

| | | |
|---|---|---|
| JP | 8-292189 A | 11/1996 |
| JP | 10-160728 A | 6/1998 |
| JP | 10-300643 A | 11/1998 |
| JP | 11-295194 A | 10/1999 |
| JP | 2000-258308 A | 9/2000 |
| JP | 2007-170979 A | 7/2007 |
| WO | 03/068398 A1 | 8/2003 |
| WO | 2005/075984 A1 | 8/2005 |
| WO | 2010/026913 A1 | 3/2010 |

OTHER PUBLICATIONS

International Search Report dated Nov. 11, 2014, issued by the International Searching Authority in corresponding International Application No. PCT/JP2014/004215.

Communication dated Mar. 22, 2017 issued by the European Patent Office in the counterpart application No. 14839073.5.

* cited by examiner

STOOL COLLECTION CONTAINER

CROSS REFERENCE TO RELATED APPLICATIONS

This application is a National Stage of International Application No. PCT/JP2014/004215 filed Aug. 19, 2014, claiming priority based on Japanese Patent Application No. 2013-174530 filed Aug. 26, 2013, the contents of all of which are incorporated herein by reference in their entirety.

TECHNICAL FIELD

The present invention relates to a stool collection container for collecting stool for stool inspection.

BACKGROUND ART

Conventionally, as a stool collection container for collecting stool for stool inspection (scatoscopy), various types of stool collection container have been proposed. Many of these are provided with a lid body provided with a stool collection rod having a helical groove in its front end side and a container body accommodating a storage solution (see Patent Document 1, for example).

In such types of stool collection container, when collecting stool, the lid body is detached, and by, for example, sticking the stool collection rod into the stool, the stool is scraped off in a helical groove provided in its front end side, and then the stool collection rod is returned to the inside of the container, and the container is sealed by the lid body. As a result, the collected stool is suspended in a storage solution accommodated within the container body. The suspension containing the stool is filtered so as to inspect the stool. In order to conduct accurate inspection, it is required to allow a constant amount of stool to be suspended in a storage solution, i.e. it is required not to allow the amount of stool suspended in a storage solution to be too large or too small.

Therefore, in many stool collection containers, when returning a stool collection rod to which stool is attached to the inside of the container body, the stool collection rod is inserted through a scraping part formed by providing a partition wall in the inside of the container body or by other methods, thereby to remove excess stool. As a result, a constant amount of stool can be collected.

RELATED ART DOCUMENT

Patent Document

Patent Document 1: JP-A-07-12808

SUMMARY OF THE INVENTION

Problems to be Solved by the Invention

Figure 9:
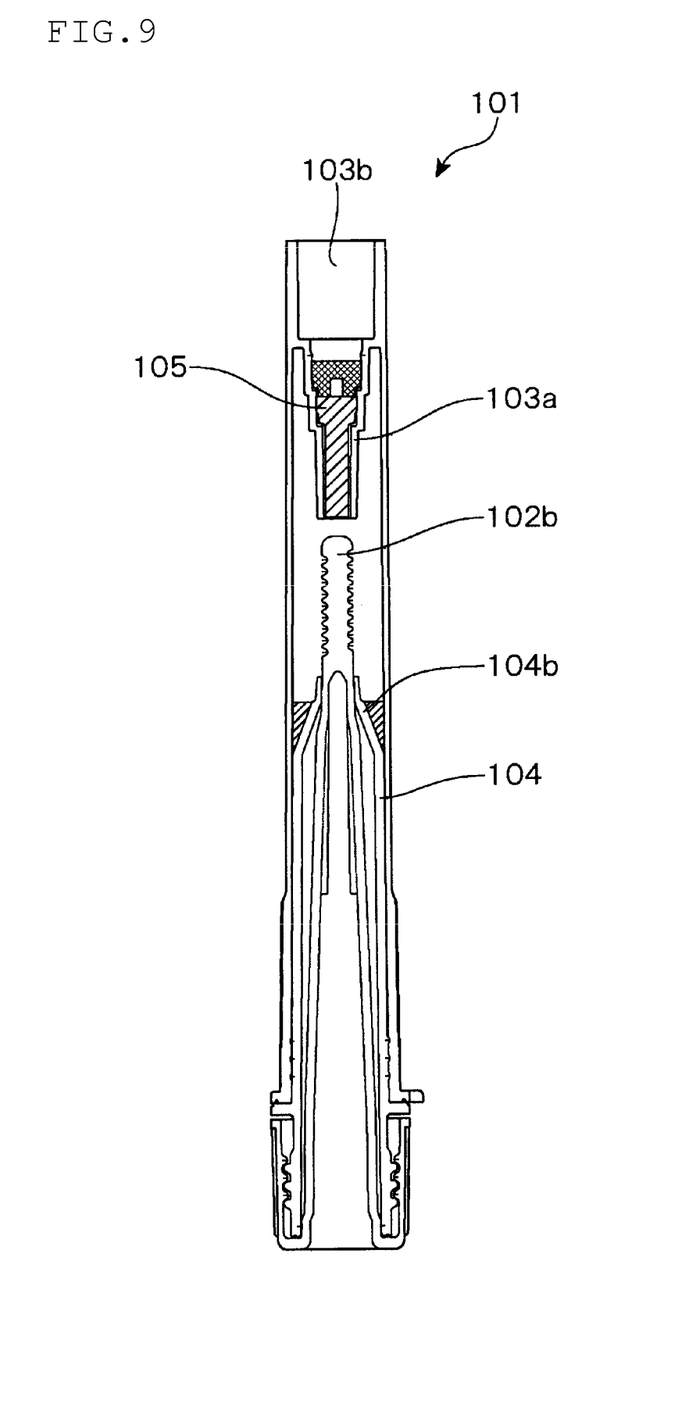
FIG. 9 is an explanatory view showing a referential example of a stool collection container.

Here, FIG. 9 shows, as a reference example, a stool collection container that was invented by the inventors of the present invention in the process of completing the present invention.

Such a stool collection container 101, which has been designed to be suitable for use in an automatic inspection apparatus, has a liquid reservoir 103b in the front end thereof formed via a filter retaining part 103a. The container is then mounted in an inspection apparatus with the liquid reservoir 103b being on top, and the container is then squeezed to filter the suspension in which the stool is suspended by means of a filter 105. The filtrate is supplied to and reserved in the liquid reservoir 103b, whereby the filtrate reserved in the liquid reservoir 103b can be introduced into the inspection apparatus.

However, as a result of studies made by the inventors, it has been found that, in the stool collection container shown in FIG. 9, there may be a case where the amount of the filtrate in the liquid reservoir 103b that is introduced into an inspection apparatus is insufficient, thereby hindering accurate inspection.

Based on this finding, the inventors made further studies. As a result, the inventors have conceived that, as for a scraping part 104b that is provided in the distal end of an inner plug 104 for removing excess stool attached to a stool collection rod 102b, forming this part into a conical shape so that the stool collection rod 102b can be inserted therethrough easily may cause the above-mentioned hindrance in inspection. That is, the inventors noted that, by forming the scraping part 104b into such a conical shape, when the container is mounted in an inspection apparatus with the liquid reservoir 103b being on top, the suspension enters around the scraping part 104b (shown by diagonal lines in FIG. 9), and as a result, the liquid level of the suspension in the container is reduced. The inventors have found that such reduction in liquid level hinders supply of a sufficient amount of a filtrate to the liquid reservoir 103b when the container body is squeezed at the time of inspection, thereby hindering accurate inspection.

The present invention has been made taking the above-mentioned circumstances into consideration. An object of the present invention is, in a stool collection container having a liquid reservoir formed at the distal end of a container body, when a scraping part for removing excess stool attached to a stool collection rod is formed on an inner plug attached to the inside of the container body, to provide a stool collection container capable of suppressing the reduction in the liquid level of a suspension inside the container body during inspection without impairing the insertability of the stool collection rod into the scraping part.

Means for Solving the Problems

A stool collection container according to the present invention is a stool collection container comprising:
a lid body that seals the container and is provided with a stool collection rod for collecting stool,
a container body having a liquid reservoir formed at the distal end thereof via a filter holding part and having an open proximal end, and
an inner plug attached to the inside of the container body from the proximal end of the container body,
wherein the distal end of the inner plug has a bottom surface that is orthogonal to the longitudinal direction and, in the center of the bottom surface, a scraping part through which the stool collection rod can be inserted is provided, and
a stool collection rod guide part is formed that comprises a plurality of sloping ribs is disposed radially around the scraping part.

Advantageous Effects of the Invention

According to the present invention, in a stool collection container in which a liquid reservoir is formed at the distal end of the container body, when forming a scraping part in an inner plug to be attached to the inside of the container body in order to remove excess stool attached to the stool collection rod, reduction in liquid level of a suspension inside the container body during inspection can be suppressed without impairing the insertability of a stool collection rod into the scraping part.

BRIEF DESCRIPTION OF THE DRAWINGS

FIGS. 1A and 1B are explanatory views showing the stool collection container according the embodiment of the present invention, in which

FIGS. 5A, 5B and 5C are explanatory views showing one example of the inner plug provided in the stool collection container according to the embodiment of the present invention, in which

MODE FOR CARRYING OUT THE INVENTION

Hereinbelow, a preferred embodiment of the present invention will be explained with reference to the drawings.

Figure 1A:
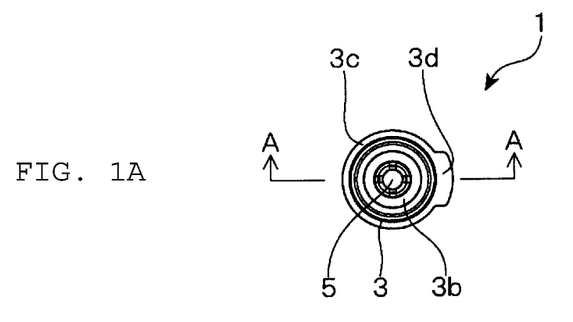
FIG. 1A is a plan view and FIG. 1B is a front view.
Figure 1B:
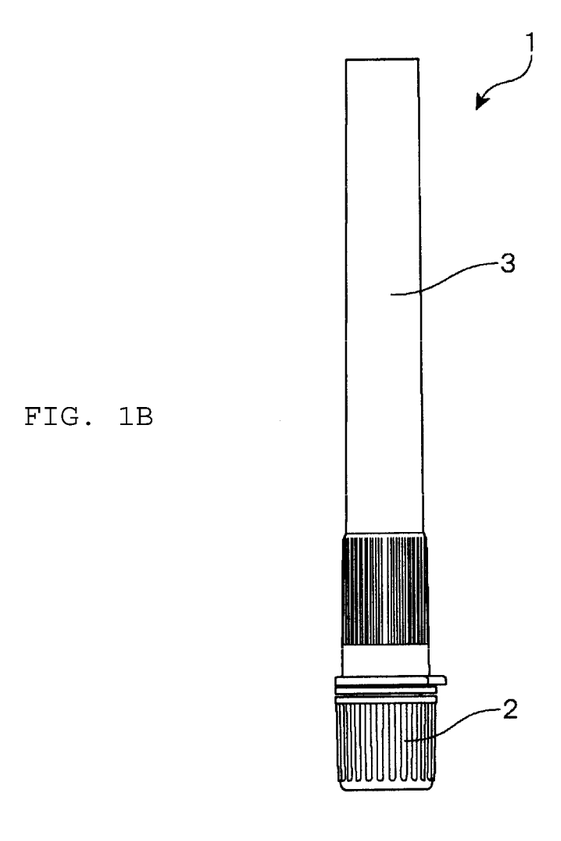
Figure 2:
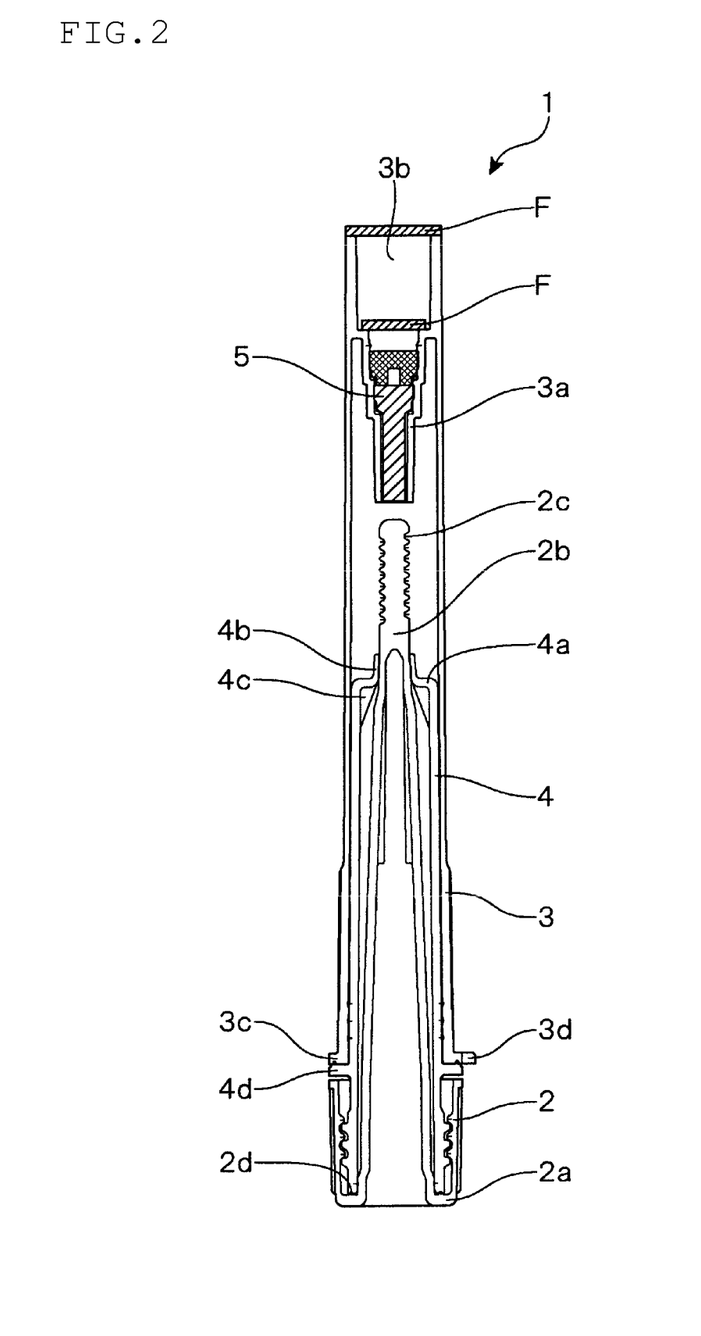
FIG. 2 is a cross-sectional view taken along line A-A in FIG. 1A.

The stool collection container 1 of this embodiment serves to collect stool when stool inspection is conducted. As shown in FIGS. 1 and 2, it is provided with a lid body 2 that seals the container, a cylindrical container body 3 accommodating a storage solution and an inner plug 4 attached to the inside of the container body 3. These members constituting the stool collection container 1 can be produced by injection molding or the like by using a thermoplastic resin, e.g. polypropylene or the like for the lid body 2, polypropylene, polyethylene or the like for the container body 3 and the inner plug 4.

Figure 3:
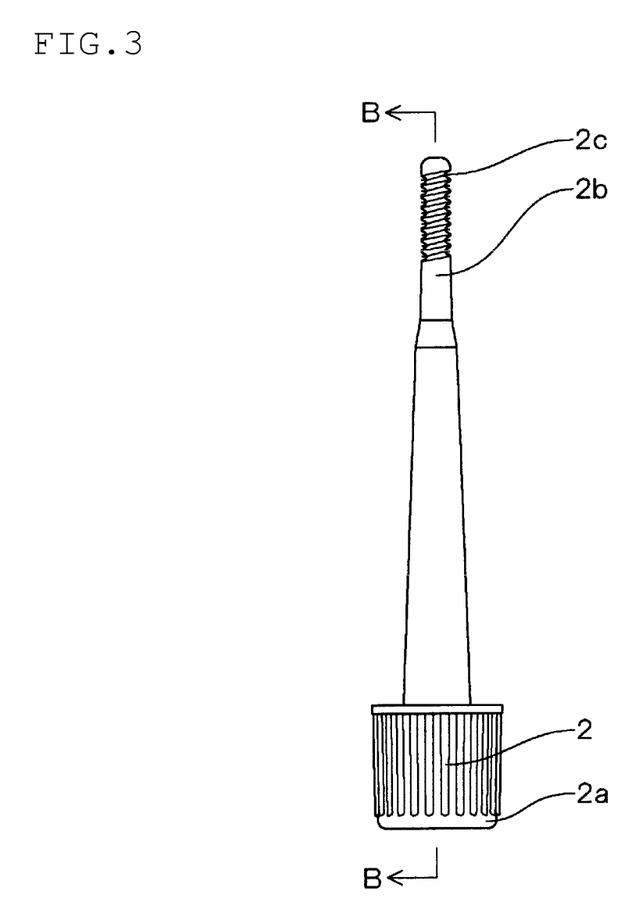
FIG. 3 is an explanatory view showing one example of the lid body provided in the stool collection container according to the embodiment of the present invention.
Figure 4:
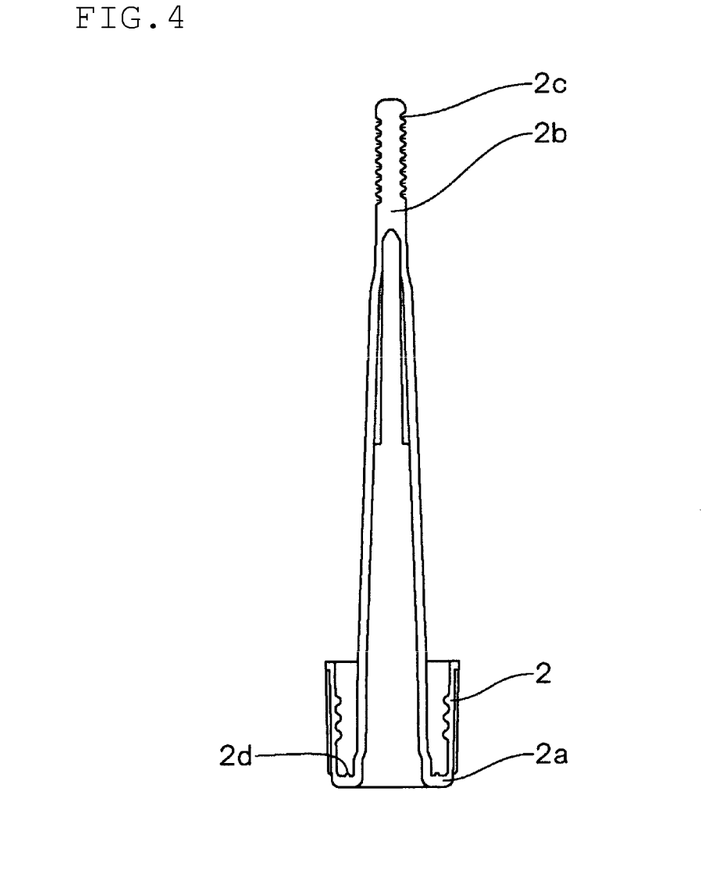
FIG. 4 is a cross-sectional view taken along line B-B in FIG. 3.

As shown in FIGS. 3 and 4, the lid body 2 of the stool collection container 1 has a stool collection rod 2b for collecting stool together with a lid body 2a that seals the container. A helical groove 2c helically engraved is formed at the front end side of the stool collection rod 2b. In order to collect stool by means of the stool collection rod 2b, the lid body 2 is detached from the inner plug 4 attached to the inside of the container body 3, and by, for example, sticking the stool collection rod 2b into the stool, the stool is scraped off in the helical groove 2c. After collecting the stool, the lid body 2 is again attached to the inner plug 4 and the stool collection rod 2b is returned to the inside of the container, and the collected stool is suspended in a storage solution accommodated in the container body 1.

In this embodiment, the helical groove 2c is formed at the front end side of the stool collection rod 2b. The configuration is not limited thereto as long as stool can be collected without fail. For example, it is possible to provide a groove that is orthogonal to the axial direction and goes around the front end side of the stool collection rod 2b. Recesses or through holes in various forms may be provided in a quantity of one or more. Stool may be in various conditions (e.g. solid, soft, liquid), and in order to collect these types of stool, various stool collecting tools have been contrived.

Further, the lid body 2 of the stool collection container 1 is configured such that it seals the container by screwing using screw threads formed on the inner circumferential surface of the lid part 2a and screw threads formed on the outer circumferential surface of the inner plug 4 attached to the inside of the container body 3. The method for attaching the lid body 2 is not limited thereto. Other methods can be used as long as the container can be sealed. For example, although not shown, the lid body 2 can be attached by engagement of an annular convex part formed on the outer circumferential surface of the inner plug 4 along the circumferential direction and an annular convex part formed on the inner circumferential direction of the lid part 2a along the circumferential direction. Either one of these convex parts may be an annular concave part so as to allow the lid body 2 to be attached by engagement of this concave part and the remaining convex part.

In order to further improve sealing properties when the lid body 2 is attached to the container, as shown in the figure, it is effective to form a protruded part 2d that abuts an edge part of the inner plug 4 annularly on the inner surface of the lid part 2a.

As for the lid body 2, it is preferred that the lid part 2a and the stool collection rod 2b be integrally molded by injection molding. However, they may be molded separately. Specific configurations of the lid body 2 are not limited as long as the container can be sealed by the lid part 2a and the stool collection rod 2b is hard enough to be stuck into stool.

In order to improve visibility of stool attached to the stool collection rod 2b, it is preferred that the stool collection rod 2b be colored by a color having a high degree of brightness (e.g. white or pale colors). It is particularly preferable to color it pale green that is close to a complementary color to the color of stool (brown or yellowish brown).

In addition, as shown in FIG. 2, the container body 3 has the liquid reservoir 3b formed at the distal end thereof via a filter holding part 3a. A filter 5 is held by the filter holding part 3a. The proximal end of the container body 3 is open so as to allow the inner plug 4 to be attached to the inside of the container body 3, and is configured such that, when the inner plug 4 is attached to the inside of the container body 3, the inner circumferential surface of the container body 3 and the outer circumferential surface of the inner plug 4 are brought into close contact in a liquid-tight manner, a storage solution accommodated within the container body 3 is prevented from leaking out.

No specific limitations are imposed on the material for the filter 5 as long as it can filter undigested solid matters that hinder stool inspection and is inactive for an inspection object. For example, a porous material such as a malt filter, filter paper and a resin sintered filter and a fibrous material such as glass wool, absorbent cotton or the like can be used. It is preferable to use a malt filter or a resin sintered filter having a predetermined fine pore diameter. These filters may be used singly or may be a stacked body of two or more filters.

In this embodiment, as shown in FIGS. 2, 5, 6 and 8, the distal end of the inner plug 4 to be attached to the inside of the container body 3 has a bottom surface 4a that is orthogonal to the longitudinal direction. In the center of the bottom surface 4a, a scraping part 4b through which the stool collection rod 2b provided in the lid body 2 can be inserted is formed. Such scraping part 4b serves to remove excess stool attached to the stool collection rod 2b when returning the stool collection rod 2b that has collected stool to the inside of the container (see FIG. 8). In the stool collection container of this embodiment, the scraping part 4b is formed as a cylindrical part opened in the center of the bottom surface 4a. The scraping part 4b is formed such that the stool collection rod 2b closely contacts the inner circumferential surface of the scraping part 4b in a light-tight manner, and excess stool is removed when the stool collection rod 2b slides on the inner circumferential surface of the scraping part 4b. Due to such configuration, it is possible to allow a constant amount of stool that fills a helical groove 2c to be suspended in a storage solution accommodated within the container body 3.

Further, in this embodiment, in order to allow the stool collection rod 2b to be inserted through the scraping part 4b easily when the stool collection rod 2b that has collected stool is returned to the inside of the container, a stool collection rod guide part formed of a plurality of sloping ribs 4c arranged radially around the scraping part 4b is formed.

Figure 5A:
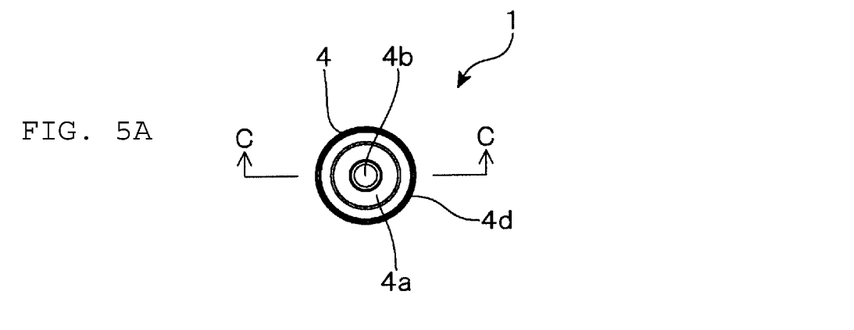
FIG. 5A is a plan view.
Figure 5B:
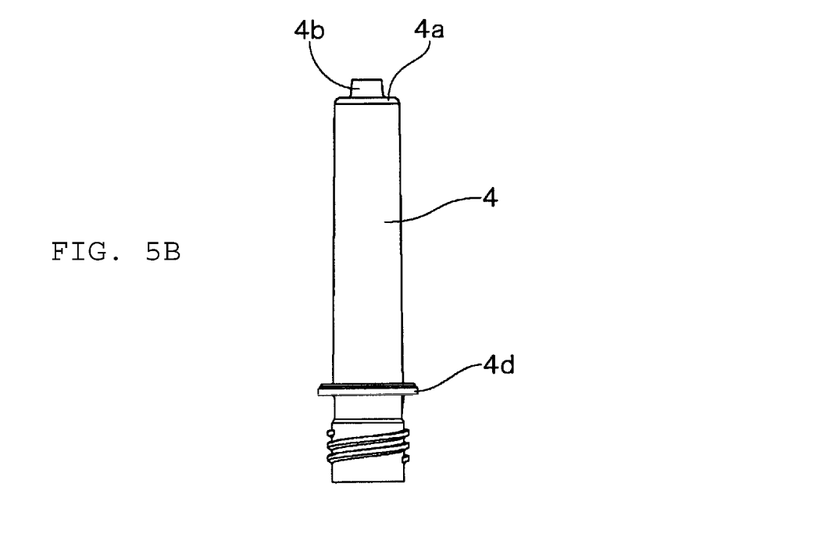
FIG. 5B is a front view and FIG. 5c is a bottom view.
Figure 5C:
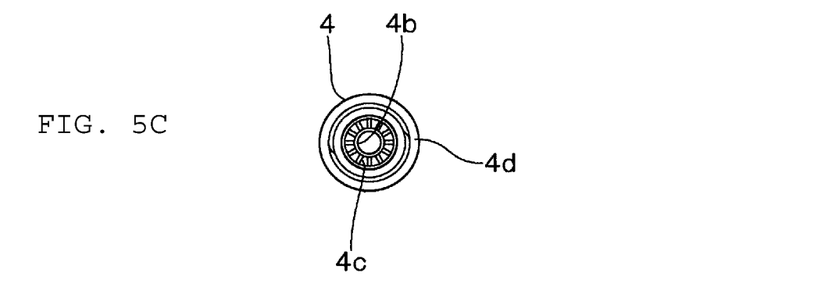
Figure 7:
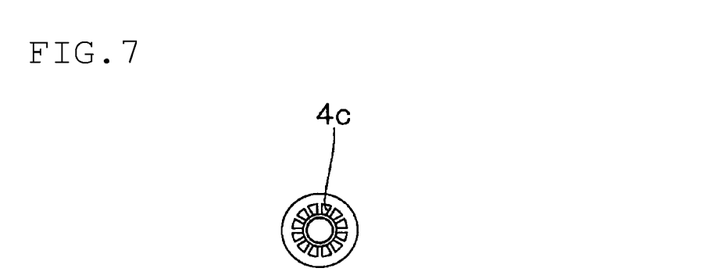
FIG. 7 is a cross-sectional view taken along line D-D in FIG. 6.

It is preferable to form plural sloping ribs 4c at equal intervals so as to realize stable guidance of the stool collection rod 2b to the scraping part 4b (see FIGS. 5c and 7).

Figure 6:
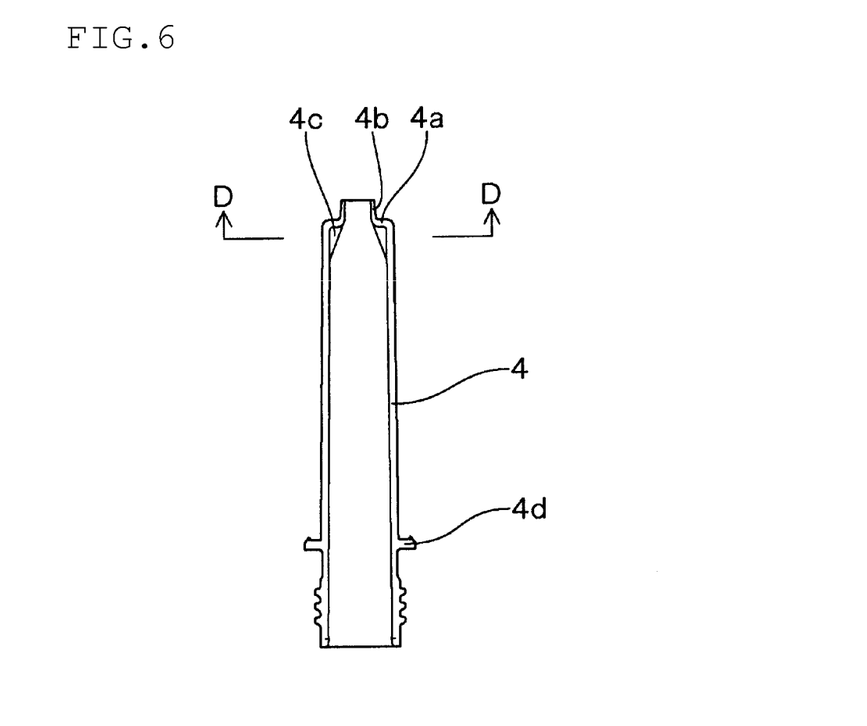
FIG. 6 is a cross-sectional view taken along line C-C in FIG. 5A.
Figure 8:
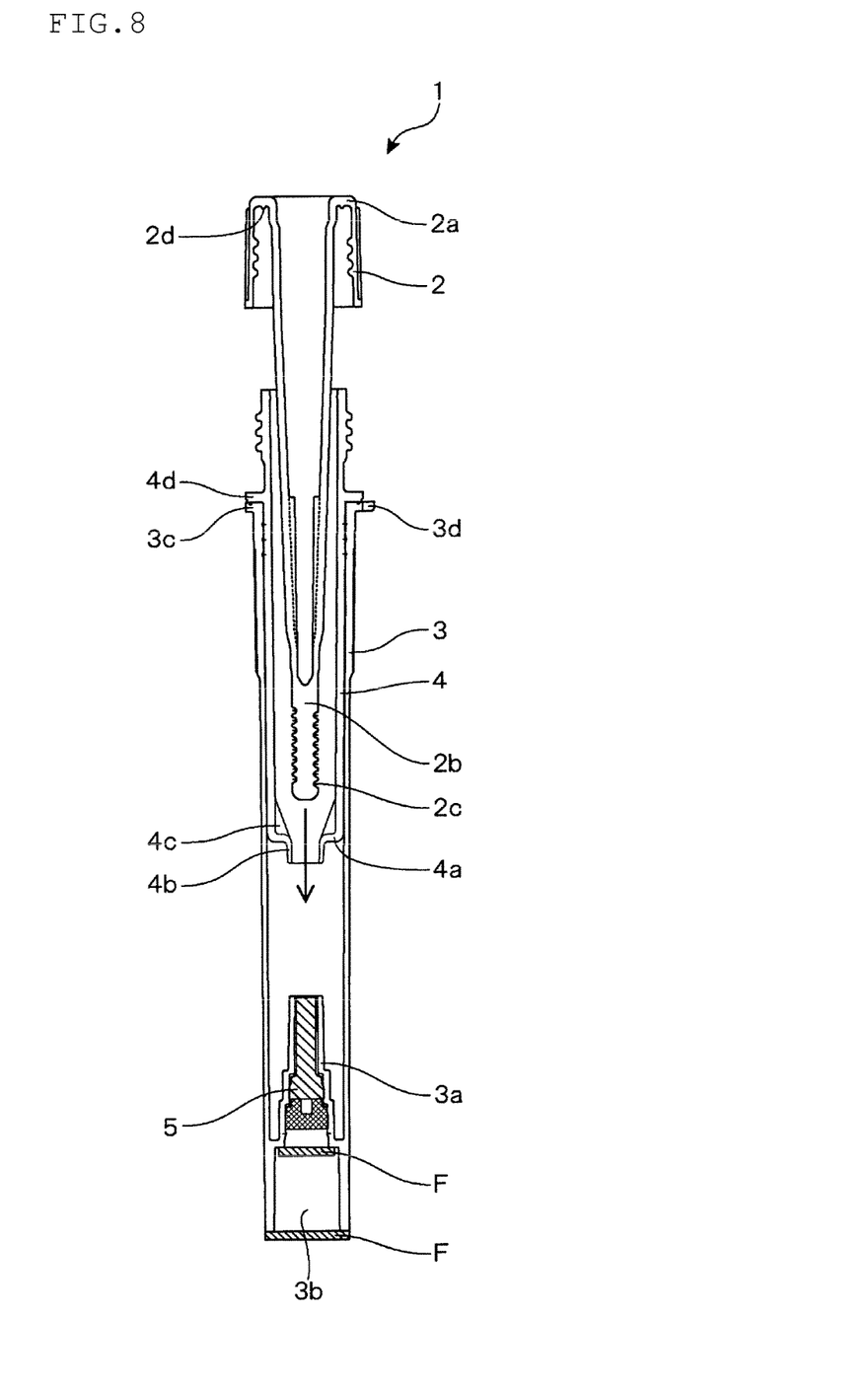
FIG. 8 is an explanatory view for explaining an operation of returning the lid body to the container body in the stool collection container according to the embodiment of the present invention.

As shown in FIGS. 2, 6 and 8, in the stool collection container 1 of this embodiment, the sloping rib 4c is formed in a triangle having a side that rises obliquely from the circumferential edge of the scraping part 4b. However, the shape thereof is not particularly limited as long as it can guide the stool collection rod 2b to the scraping part 4b.

In order to guide the stool collection rod 2b to the scraping part 4b, a part surrounding the scraping part 4b may be in a conical shape. However, such configuration makes the bottom surface 4a side of the inner plug 4 thick. As a result, the amount of a resin required for molding may be increased, or a longer time may be taken for cooling, leading to lowering in production speed. Further, the shrinkage quantity of the resin increases at the time of cooling, thereby adversely affecting dimensional stability. By disposing a plurality of the sloping ribs 4c radially (see FIGS. 5(c) and 7), and by forming the stool collection rod guide part by providing a space between adjacent sloping ribs 4c, such disadvantages can be effectively eliminated.

The stool collection container 1 of this embodiment is preferable for conducting stool inspection in accordance with inspection items by using an inspection apparatus. After suspending the stool collected by the stool collection rod 2b in a storage solution accommodated within the container body 3, the container is mounted in the apparatus with the distal end of the container body 3 in which the liquid reservoir 3b is formed being on top. Then, at the time of inspection, the container body 3 is squeezed and a suspension obtained by suspending the stool in a storage solution is filtered by the filter 5, the filtrate is then supplied to and reserved in the liquid reservoir 3b, whereby it can be introduced into the inside of the inspection apparatus.

As shown in FIG. 2, in the stool collection container of this embodiment, the bottom part and the upper part of the liquid reservoir 3b of the container body 3 can be sealed by means of a film material F or the like. Due to such a configuration, before using the container in inspection, the sealing properties of the container can be ensured, and at the time of inspection, by piercing the film material F or the like, the suspension in the container is supplied to and reserved in the liquid reservoir 3b for inspection. As for the film material F, it is preferable to use a laminated film obtained by stacking aluminum foil and a thermoplastic resin such as polypropylene and polyethylene. The film material F is welded to the liquid reservoir 3b. Further, although not particularly shown, instead of the film material F, sealing may be conducted by means of a lid body that is screwed or engaged with the distal end of the container body 3. When such a lid body is used, for introducing a suspension, the lid body is detached in advance. Alternatively, the middle part of the lid body is made thin, and a suspension is introduced by piercing this thin part.

As the storage solution in which the collected stool is suspended, any solution can be used as long as it is suited for stool inspection. According to need, an additive such as a buffer, salts, a stabilizer, a preservative, a colorant and a deodorizing agent may be added. The amount of the storage solution accommodated within the container body 3 is appropriately adjusted in accordance with the concentration of suspended stool required for stool inspection. For example, when collecting 5 mg of stool, a dilution ratio of 400 times can be obtained by allowing the amount of the liquid to be 2 ml.

In this embodiment, by allowing the distal end of the inner plug 4 to be attached to the inside of the container body 3 to have the above-mentioned configuration, when the liquid reservoir 3b at the distal end of the container body 3 is made on top during inspection, reduction in liquid level of the suspension inside the container that occurs in the above-mentioned stool collection container shown in FIG. 9 can be suppressed without impairing the insertability of the stool collection rod 2b into the scraping part 4b. Specifically, since the bottom surface 4a of the distal end of the inner plug 4 is orthogonal to the longitudinal direction, unlike the stool collection container shown in FIG. 9, no gap is generated around the scraping part 4b, and hence reduction in liquid level for the portion thereof can be prevented.

Therefore, when a suspension obtained by suspending stool in a storage solution is supplied to the liquid reservoir 3b by squeezing the container, a sufficient amount of a filtrate obtained by filtration with the filter 5 can be reserved in the liquid reservoir 3b. As a result, when conducting stool inspection by an inspection apparatus, a disadvantage that inspection is hindered due to an insufficient amount of the filtrate introduced into the apparatus can be effectively eliminated.

In the stool collection container 1 shown in FIGS. 1A and 1B, the inner plug 4 is attached to the inside of the container body 3 by welding a flange part 3c formed along an edge part of the opening at the proximal end of the container body 3 and a projection part 4d formed along the circumferential direction of a predetermined position on the outer circumferential surface of the inner plug 4 by an appropriate means such as ultrasonic welding. Further, by forming a convex part 3d that partially protrudes from the peripheral edge of the flange part 3c in the flange part 3c of the container body 3, the convex part not only prevents the stool collection container 1 from rolling but also it serves to allow the stool collection container 1 to be positioned when mounting the container in an inspection apparatus.

In the stool collection container 1 shown in FIGS. 1A and 1B, the convex part 3d is formed in the peripheral edge of the flange part 3c of the container body 3. However, a similar convex part may be formed such that it protrudes from a projection part 4d of the inner plug 4. The convex part may be formed in at least one of the flange part 3c and the projection part 4d.

Hereinabove, the present invention have been explained with reference to preferable embodiments. The present invention is not limited to the above-mentioned embodiments, and it is needless to say various modifications are possible with the scope of the invention.

INDUSTRIAL APPLICABILITY

As mentioned above, the present invention can be used as a stool collection container for collecting stool when conducting stool inspection.

EXPLANATION OF REFERENTIAL NUMERALS

1. Stool collection container
2. Lid body
2a. Lid part
2b. Stool collection rod
3. Container body
3a. Filter holding part
3b. Liquid reservoir
3c. Flange part
3d. Protruded part
4. Inner plug
4a. Bottom surface
4b. Scraping part
4c. Sloping rib
4d. Projection part

The invention claimed is:

1. A stool collection container comprising:
   a lid body that seals the container and is provided with a stool collection rod for collecting stool,
   a container body which has a liquid reservoir formed at a distal end thereof via a filter holding part and in which a proximal end of the container body is open, and
   an inner plug attached to the inside of the container body from the proximal end of the container body,
   wherein the lid body seals the container by attaching the lid body to the inner plug,
   the distal end of the inner plug has a bottom surface that is orthogonal to a longitudinal direction of the inner plug,
   the bottom surface of the inner plug has a scraping part through which the stool collection rod can be inserted and which opens in the center of the bottom surface, and
   a stool collection rod guide part that comprises a plurality of sloping ribs disposed radially around the scraping part is formed inside of the bottom surface of the inner plug.

2. The stool collection container according to claim 1, wherein the container body has a flange part formed along an edge of an opening of the proximal end of the container body,
   the inner plug has a projection part formed along a circumferential direction on the outer circumferential surface of the inner plug, and
   a convex part partially protruding from a peripheral edge of at least one of the flange part and the projection part is formed in at least one of the flange part and the projection part.

* * * * *